US012359750B1

United States Patent
Heisler, III et al.

(10) Patent No.: US 12,359,750 B1
(45) Date of Patent: Jul. 15, 2025

(54) WIRE HARNESS

(71) Applicants: Joseph F. Heisler, III, Toms River, NJ (US); Michael Heisler, Toms River, NJ (US); Christopher Lanagan, Manchester, NJ (US)

(72) Inventors: Joseph F. Heisler, III, Toms River, NJ (US); Michael Heisler, Toms River, NJ (US); Christopher Lanagan, Manchester, NJ (US)

(73) Assignees: Joseph F. Heisler, III, Toms River, NJ (US); Michael Heisler, Toms River, NJ (US); Christopher Lanagan, Toms River, NJ (US)

(*) Notice: Subject to any disclaimer, the term of this patent is extended or adjusted under 35 U.S.C. 154(b) by 0 days.

(21) Appl. No.: 18/402,027

(22) Filed: Jan. 2, 2024

(51) Int. Cl.
  *F16L 3/22* (2006.01)
  *A61B 5/30* (2021.01)
  *A61B 5/332* (2021.01)
  *F16L 3/133* (2006.01)

(52) U.S. Cl.
  CPC .............. *F16L 3/222* (2013.01); *A61B 5/303* (2021.01); *A61B 5/332* (2021.01); *F16L 3/133* (2013.01)

(58) Field of Classification Search
  CPC .......... F16L 3/222; F16L 3/133; A61B 5/302; A61B 5/332
  USPC ......................................................... 248/49
  See application file for complete search history.

(56) References Cited

U.S. PATENT DOCUMENTS

| | | | | |
|---|---|---|---|---|
| 3,212,647 A * | 10/1965 | Meyer | A47G 25/1457 D6/315 |
| 3,518,791 A * | 7/1970 | Carson | A01G 17/08 248/339 |
| 5,107,996 A * | 4/1992 | Whittaker | A47G 25/1457 211/116 |
| 5,582,334 A * | 12/1996 | Blazer | A47G 25/1457 223/86 |
| 6,247,963 B1 * | 6/2001 | Rattner | A61B 90/00 439/502 |
| 7,093,807 B2 * | 8/2006 | Wylie | H02G 3/32 248/68.1 |
| 10,433,926 B2 * | 10/2019 | Recanati | A61B 50/20 |
| 10,767,685 B2 * | 9/2020 | Bauer | F16B 45/00 |
| 2006/0031988 A1 | 2/2006 | Morse | |
| 2020/0121211 A1 | 4/2020 | Tutino | |
| 2021/0327612 A1 * | 10/2021 | Park | H01B 7/368 |

FOREIGN PATENT DOCUMENTS

| CN | 2812858 Y | 9/2006 |
|---|---|---|
| CN | 203988042 U | 12/2014 |
| CN | 110477903 A | 11/2019 |
| CN | 212489917 U | 2/2021 |
| CN | 213488871 U | 6/2021 |

* cited by examiner

*Primary Examiner* — Anita M King
(74) *Attorney, Agent, or Firm* — MOSER TABOA

(57) ABSTRACT

Methods and apparatus for organizing wires, each wire having a terminal connector at an end of the wire. In some embodiments, the apparatus includes: an elongated body comprising a plurality of holes, wherein at least one hole of the plurality of holes is configured to pass through and retain a terminal connector disposed at the end of a wire; and a retainer attached to the elongated body, the retainer configured to removably attach the apparatus to a structure.

10 Claims, 2 Drawing Sheets

WIRE HARNESS

FIELD

This present disclosure relates to a wire and cable organization, and more specifically for the organization of medical equipment wires, such as EKG wires.

BACKGROUND

Wires are often used in medical facilities to connect between sensors on a patient and sensor monitoring equipment. In some instances, large numbers of wires may be connected between the patient and the equipment. Often, the wires may need to be disconnected and reconnected, such as when equipment is changed or when a patient is moved. When the wires become disconnected, the loose wires may be left on a patient bed, left on the floor, or draped over the equipment. Also, the loose wires may become tangled with one another making re-connection of the wires more time consuming.

Thus, it is desirable to improve organization of wires, especially in the medical environment.

SUMMARY

Methods and apparatus for organizing wires are provided herein. In some embodiments, an apparatus for organizing wires is provided wherein each wire has a terminal connector at an end of the wire. The apparatus comprises: an elongated body comprising a plurality of holes, wherein at least one hole of the plurality of holes is configured to pass through and retain a terminal connector disposed at the end of a wire; and a retainer attached to the elongated body, the retainer configured to removably attach the apparatus to a structure.

In some embodiments, a method of organizing wires is provided wherein each wire has a terminal connector at an end of the wire. The method includes: providing an apparatus for organizing the wires, the apparatus comprising: an elongated body comprising a plurality of holes, wherein at least one hole of the plurality of holes is configured to pass through and retain a terminal connector of a wire; and a retainer attached to the elongated body, the retainer configured to removably attach the apparatus to a structure, and inserting at least the terminal connector into the at least one hole of the elongated body.

Other and further embodiments of the present disclosure are described below.

BRIEF DESCRIPTION OF THE DRAWINGS

Embodiments of the present disclosure, briefly summarized above and discussed in greater detail below, can be understood by reference to the illustrative embodiments of the disclosure depicted in the appended drawings. However, the appended drawings illustrate only typical embodiments of the disclosure and are therefore not to be considered limiting of scope, for the disclosure may admit to other equally effective embodiments.

Figure 1:
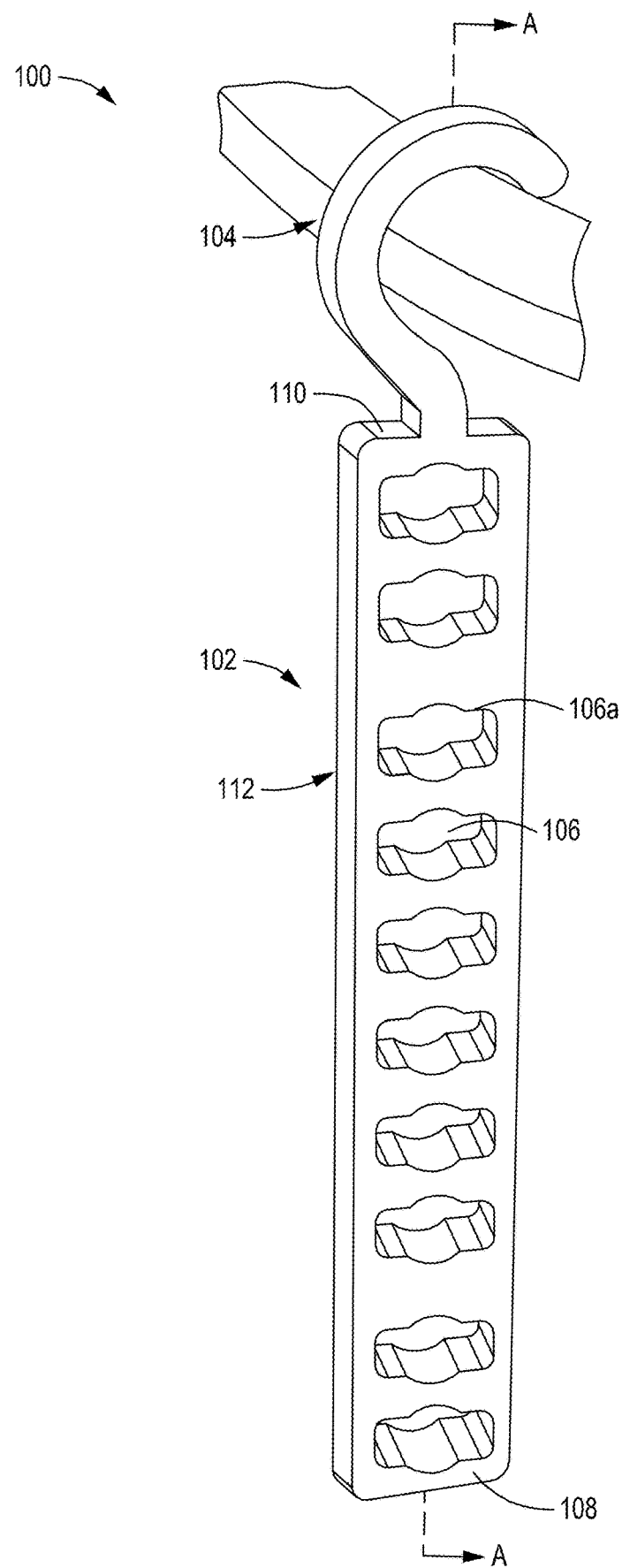
FIG. 1 shows an apparatus for organizing wires in accordance with some embodiments of the present disclosure.

To facilitate understanding, identical reference numerals have been used, where possible, to designate identical elements that are common to the figures. The figures are not drawn to scale and may be simplified for clarity. Elements and features of one embodiment may be beneficially incorporated in other embodiments without further recitation.

DETAILED DESCRIPTION

In some embodiments, and as shown in FIG. 1, an apparatus (e.g., a wire harness) 100 may be provided for organizing or otherwise arranging wires (e.g., wires 200 shown in FIG. 2) that have a terminal connector (e.g., terminal connector 202) at an end of the wires 200. The wires 200 may be EKG wires that have various terminal connectors 202 for connecting to at least one of EKG equipment or electrodes. In some embodiments, and as shown in FIG. 1, the apparatus 100 may include an elongated body 102 comprising a plurality of holes 106 (10 holes are shown in FIG. 1). The holes 106 may be arranged in any pattern. For example, the holes 106 may be arranged in one or more columns or rows. In some embodiments, and as shown in FIG. 1, the holes 106 may be stacked in a column as shown in FIG. 1. In some embodiments, the holes 106 are fully closed and are defined by respective closed edges 106a. Although a continuous edge is shown in FIG. 1, it will be appreciated that in some embodiments, the edge 106a may be discontinuous, and may have, for example, segments or serrations to operatively grip portions of the wire 200 and/or terminal connector 202.

At least one hole 106 of the plurality of holes may be configured to pass through and retain a terminal connector 202 disposed at the end of a wire 200, such an EKG wire. In some embodiments, the shape of at least one of the holes 106 may be configured to pass through and retain one or more types of terminal connectors 202. Configuring the hole(s) 106 to receive and retain multiple different types of terminal connectors 202 can provide a more universal fit for different types of terminal connectors. For example, commercially available EKG wires have different types of terminal connectors (e.g., round profile, square or prismatic profile, etc.).

In some embodiments, the elongated body 102 may be flexible. In some embodiments, the elongated body 102 may be formed of a flexible material, such as a plastic or thermoplastic elastomer, rubber, or silicone. In some embodiments, the holes 106 may be slightly expandable to stretch and compress against an inserted terminal connector 202 to facilitate retention of the terminal connector in the hole 106. The elongated body 102 may be antimicrobial or have an antimicrobial coating.

Figure 3:
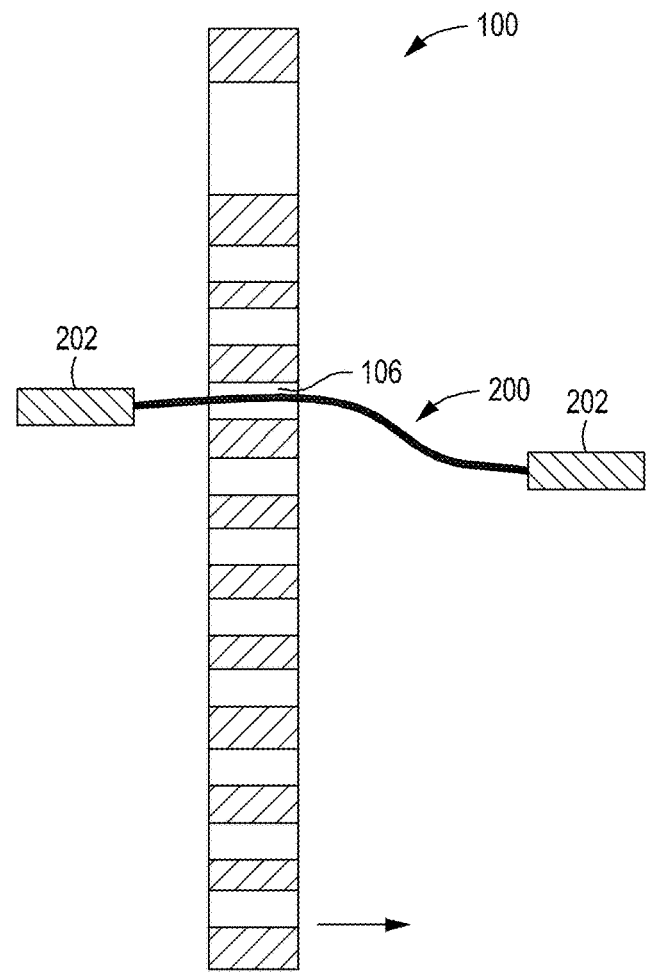
FIG. 3 shows the apparatus in FIG. 2 during relative movement between the apparatus and the wire in accordance with some embodiments of the present disclosure.

In some embodiments, at least one hole 106 may be configured to permit free relative movement between the at least one hole 106 and the wire 200 when the wire 200 is inside the hole, as is shown, for example, in FIG. 3. In some embodiments, and as shown in FIG. 3, during use, the terminal connector 202 of a wire 200 may be inserted fully through one of the holes 106 so that the wire is inside the hole 106. In some embodiments, the hole 106 may have a larger size (e.g., diameter) than an outer diameter of the wire 200 to permit free relative movement between the at least one hole 106 and the wire 200. When multiple wires 200 are inside respective holes 106, the apparatus 100 can be slid along the wires 200 in one direction to thereby trace and organize the wires. It will be appreciated that "free relative movement" refers to the ability of a user to manually move the apparatus and the wire relative to one another and does not imply that there is no friction or resistance to motion that may be caused by contact between a respective wire and the apparatus.

In some embodiments, the at least one hole 106 may be configured to resist free relative movement between the at least one hole 106 and the wire 200 when the wire is inside the hole. This latter feature may be useful to retain the apparatus at a user-set location along the wires 200. For example, in at least some embodiments, the hole 106 may have a size (e.g., diameter) that is less than an outer diameter of the wire 200, but may still be configured to permit a user to manually move the apparatus 100 relative to the wire 200. In some examples, the diameter of the hole 106 may be slightly smaller than the outer diameter of the wire 200 so that the wires are slightly compressed in the hole to retain a position of apparatus 100 relative to the wire 200. The compressive force may be low enough to permit a user to still manually slide the wire 200 in the hole 106, such as towards a terminal connector 202.

In some embodiments, and as shown in FIG. 1, the apparatus 100 may also include a retainer 104 attached to the elongated body 102. In some embodiments, and a shown in FIG. 1, the retainer 104 may include a hook. The retainer 104 may be configured to removably attach the apparatus 100 to a structure (e.g., EKG equipment, hospital bed frame, etc.). In some embodiments, the retainer 104 may be magnetic to allow attachment of the apparatus 100 to a ferromagnetic surface. In some embodiments, and a shown in FIG. 1, the retainer 104 may be located at an end 110 of the elongated body 102. In FIG. 1, the retainer 104 is located on a relatively short side of the elongated body 102 so that the holes 106 extend vertically when the apparatus 100 is hung from the hook 104. In some embodiments, the retainer 104 may be located at another end 108 of the elongated body 102 or at another location on the body, such as at an intermediate location (e.g., midpoint) 112 between the ends 108, 110 of the elongated body 102. In some embodiments, the retainer 104 may be located along the longer side of the elongated body 102 so that the holes 106 extend horizontally when the apparatus 100 is hung.

In some embodiments, the elongated body 102 and the retainer 104 may be a monolithic structure. For example, in some embodiments, the elongated body 102 and the retainer 104 may be formed entirely as a single piece, and may be formed from one material, such as a plastic or thermoplastic elastomer.

Figure 2:
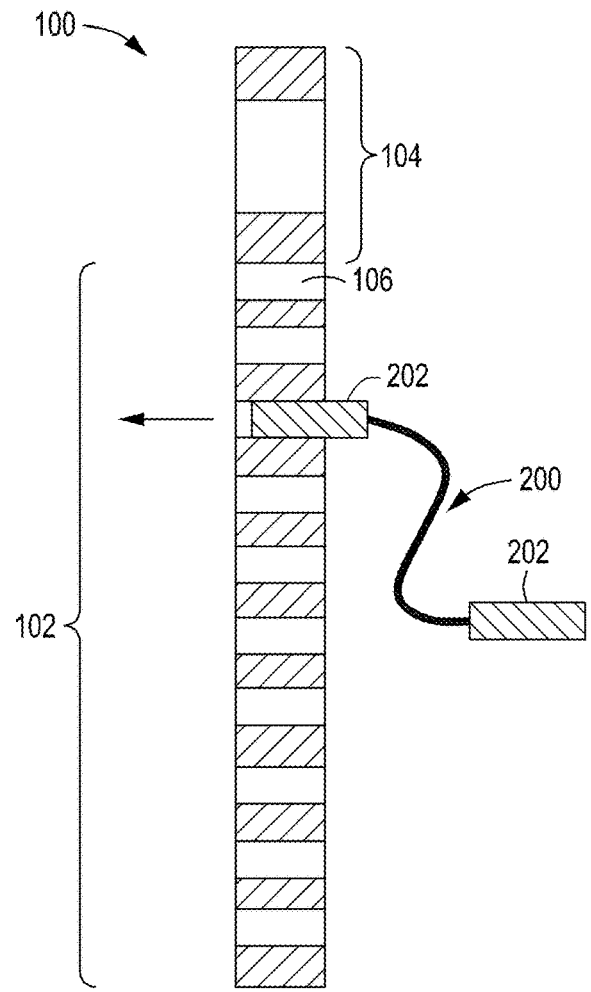
FIG. 2 shows the apparatus along section A-A in FIG. 1 while a terminal connector of a wire is inserted into a hole of the apparatus in accordance with some embodiments of the present disclosure.

According to some embodiments, a method of organizing or otherwise arranging wires having a terminal connector at an end of the wires, such as wires 200, may include providing an apparatus for organizing or otherwise arranging wires, such as apparatus 100, and inserting at least the terminal connector 202 into the at least one hole 106 of the elongated body 102 as shown, for example, in FIG. 2. In some embodiments, the method may include inserting the terminal connector 202 fully though the at least one hole 106 so that the wire 200 is inside the hole, as shown for example in FIG. 3. In some embodiments, the method may include moving the apparatus 100 relative to the at least one wire 200 with the wire 200 inside the hole 106, as indicated by the arrow in FIG. 3.

The following is an example of a method of using the apparatus 100 in the context where the wires 200 are EKG wires having terminal connectors 202 at both ends of the wires 200. In one example, terminal connectors 202 of each EKG wire are inserted into at least one hole 106 of the elongated body 102 of the apparatus 100 and the terminal connectors 202 at the other ends of the EKG wires 200 are connected to an EKG machine. A user (e.g. a nurse) may insert the terminal connector 202 of the EKG wires through the holes 106 so that the wires 200 are in the holes 106. The user may then slide the apparatus 100 (e.g., away from the terminal connectors and toward the EKG machine) along the wires 200 and connect each terminal connector 202 to an EKG lead on a patient. The process may be performed in reverse to disconnect the EKG wires from the patient.

For example, the user may disconnect each EKG wire 200 from the patient, slide the apparatus 100 along the wires 200 towards the disconnected ends of the EKG wires 200, and then insert each disconnected terminal connector 202 of the EKG wires into corresponding holes 106 of the elongated body 102 to retain the terminal connectors 202 in an organized manner to facilitate future reconnection.

The invention claimed is:

1. A method of organizing wires, each wire having a terminal connector at an end of the wire, the method comprising:
  providing an apparatus for organizing the wires, the apparatus comprising:
    an elongated body comprising a plurality of holes, wherein at least one hole of the plurality of holes is configured to pass through and retain a terminal connector of a wire; and
    a retainer attached to the elongated body, the retainer configured to removably attach the apparatus to a structure; and
  inserting at least the terminal connector into the at least one hole of the elongated body.

2. The method of claim 1, wherein the at least one hole is configured to permit free relative movement between the at least one hole and the wire, and further comprising sliding the apparatus along the wire.

3. The method of claim 1, wherein the at least one hole is configured to pass through and retain a terminal connector of an EKG wire.

4. The method of claim 1, further comprising inserting the terminal connector fully through the at least one hole so that the wire is inside the at least one hole and sliding the apparatus along the wire.

5. The method of claim 1, wherein the elongated body and the retainer are formed from plastic or thermoplastic elastomer.

6. The method of claim 1, wherein the plurality of holes are defined by a closed edge.

7. The method of claim 1, wherein at least one of the elongated body or the retainer are antimicrobial or have an antimicrobial coating.

8. The method of claim 7, wherein the retainer is located at an end of the elongated body.

9. The method of claim 1, wherein the elongated body is flexible.

10. The method of claim 1, wherein the retainer is formed as a hook.

* * * * *